United States Patent [19]

Waddell

[11] 4,450,832
[45] May 29, 1984

[54] BODY WEIGHT SUPPORT SYSTEM

[76] Inventor: Thomas P. Waddell, 1306 Broadview W., Downingtown, Pa. 19335

[21] Appl. No.: 411,404

[22] Filed: Aug. 25, 1982

[51] Int. Cl.³ ............................................. A61F 3/00
[52] U.S. Cl. ................................. 128/80 G; 2/22; 128/80 C
[58] Field of Search ................ 128/80 R, 80 C, 80 G, 128/87 R, 88, 89; 2/22, 24

[56] References Cited

U.S. PATENT DOCUMENTS

3,799,159 3/1974 Scott ............................... 128/80 C
3,928,872 12/1975 Johnson ........................ 128/80 C X Primary Examiner—John D. Yasko
Attorney, Agent, or Firm—Caesar, Rivise, Bernstein & Cohen, Ltd.

[57] ABSTRACT

A body weight support system for skiing or other physical activities including at least one leg brace. The brace consists of a pair of parallel elongated tubular members interconnected by a cable, a plurality of cylindrical segment members are interposed in the knee section of the brace with the cable extending therethrough to form non-resilient flexure means for allowing the brace to bend with the knee upon flexure of the knee. Tensioning means are provided for the cable to establish the tension therein and hence establish a maximum angle deflection of the flexure means. The brace and flexure means are non-resilient so that once the maximum angle is attained the brace resists further deflection. The brace also includes fabric means spanning the tubular members for supporting the legs of the wearer. Strap means are provided for securing the brace to the leg and to a boot (e.g., ski boot).

27 Claims, 15 Drawing Figures

BODY WEIGHT SUPPORT SYSTEM

BACKGROUND OF THE INVENTION

This invention relates generally to support structures, and more particularly, to systems for supporting the body weight of a person to facilitate various recreational and vocational activities.

Various braces have been proposed in the patent literature to provide leg support for persons. Some braces have even been proposed for wearing on a person's legs to facilitate snow skiing. For example, in U.S. Pat. No. 3,928,872 (Johnson), there is disclosed a pair of devices, each of which is securable to a leg of the skier, to provide flexural knee and leg support. Each device includes an upper support sleeve positioned about the skier's leg above the knee and interconnected by a spring to lower support sleeve which is positioned about the skier's leg below the knee. The devices are ostensibly arranged so that the skier can assume a crouched position with part of the upper body weight being supported other than by the skier's knees. The springs are resilient beam springs. While the stated objective of the devices in the Johnson patent is to reduce weight load on the knees, absorb shock and reduce the strain when the knee flexes, the use of resilient spring means appears to inherently produce an oscillatory or bouncing effect on the skier's body as the angle of his or her knee flexure changes during a ski run owing to the uneven terrain of a typical ski slope. The more rigid the spring, the more pronounced the rebounding effect will be, which effect is quite undesirable for controlled skiing. Moreover, the frequency of the springs of the Johnson patent will likely rarely match the frequency of flexure of the knee as caused by the traversal over the terrain. Thus, the device may tend to take the skier out of synchronism with the terrain, thereby also resulting in the loss of balance and control.

In U.S. Pat. No. 4,136,404 (Lange), there is disclosed a brace for a skier which includes for each leg an upper and lower brace member interconnected at the knee in a pivoting, hinged joint. Each brace includes lateral support members which are arranged to be secured to respectively the upper and lower portions of the skier's leg. The brace is arranged to be mounted on the ski boot so that when so mounted, it has the effect of transmitting lateral forces to the edge of the skier's skis, while precluding excessive lateral bending forces on the skier's legs. While the device of the Lange patent appears generally suitable for its intended purposes, it fails to provide any body weight support for the skier since it permits free and unencumbered forward and rearward flexing of the skier's legs.

U.S. Pat. No. 3,665,619 (Gray), discloses a skier leg support in the form of a contoured member adapted to be secured by a strap to the ski boot. The contoured member extends upward toward the wearer's calf so that the support stiffness is transferred upwardly onto the skier's calf, adding strength to the leg when the skier leans back on the skis during acceleration.

U.S. Pat. No. 3,678,603 (Kaufman et al), discloses a ski boot having extension means extending up from the boot to the skier's calf in a similar manner to the patent to Gray. Both the Kaufman et al and Gray patents fail to provide any body weight support for the skier.

OBJECTS OF THE INVENTION

It is a general object of the instant invention to provide a body weight support system which overcomes the disadvantages of the prior art.

It is a further object of the instant invention to provide a support system for use on a person's leg to allow unimpeded flexing of the knee up to a predetermined angle while restricting further flexing therebeyond.

It is a further object of the instant invention to provide a support system for wearing on the leg which is incorporated in a garment.

It is still a further object of the instant invention to provide a body weight support system which is particularly suitable for skiing.

These and other objects of the instant invention are achieved by providing a body weight support system to be securable to at least one leg of a person. The system comprises first support means, second support means and non-resilient, flexure means. The first support means includes a first portion extending along the thigh and terminates at its upper end immediately adjacent the buttocks-thigh interface to form a seat and terminates at its lower end adjacent the knee. The second support system includes a second portion extending along the calf and with the second support means terminating at its upper end adjacent the knee and its lower end adjacent the foot. The flexure means is located at the knee and is connected between the first and second support means to enable the person to bend the knee through an angular range up to a predetermined angle while precluding any flexure therebeyond. The first and second support means includes securement means for releasably securing said system to the leg.

Other objects and many of the attendant advantages of this invention will be readily appreciated as the same becomes better understood by reference to the following detailed description when considered in connection with the accompanying drawing wherein:

DETAILED DESCRIPTION OF THE PREFERRED EMBODIMENT

Figure 1:
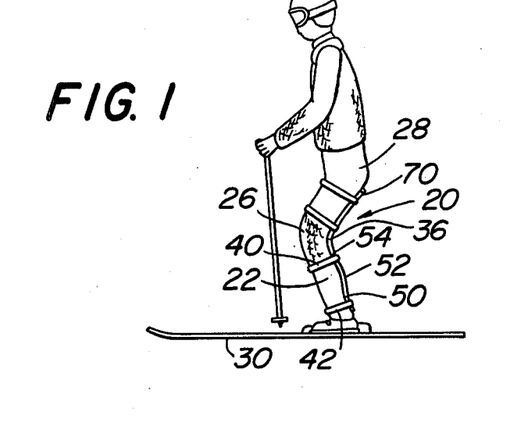
FIG. 1 is a side elevational view of a skier wearing one embodiment of the body weight support system of the instant invention.

Referring now to the various figures of the drawing wherein like reference characters refer to like parts, there is shown in FIG. 1 a snow skier wearing one embodiment of the body weight support system 20 constructed in accordance with the instant invention. A typical system 20 basically consists of a pair of braces 22, each of which is secured to a respective leg of the skier and to the ski boots 24 worn by the skier. While the system 20 usually will consist of a pair of braces, this invention contemplates a body weight support system having only a single brace, such as would be used by a one-legged skier. Even the single brace system is sufficient to provide all of the advantages of the invention for the skier. Moreover, while the remainder of this specification will be directed at the invention for use by skiers, it must be kept in mind that the system of this invention can be used for various applications where support of body weight is of importance.

As will be appreciated from the following specification, the system 20 shown herein is configured so that it can be readily adjusted to provide support for the skier so that the skier can readily assume and maintain the proper "attack" position, e.g., knees 26 bent forward of the boots 24, with the buttocks 28 centered over the boots.

Each brace 22 of the system shown in FIG. 1 is in the form of an attachment arranged for securement to an associated leg and worn over the garment on the leg. In the embodiment shown in FIG. 12, which embodiment will be described later, the system 20 is itself incorporated into a garment, e.g., pants.

Figure 2:
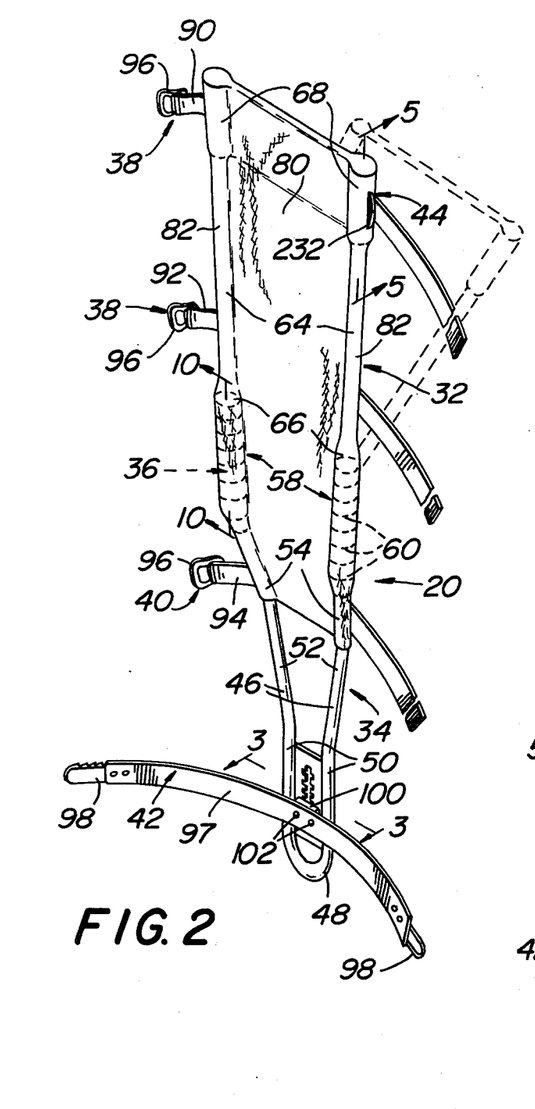
FIG. 2 is an enlarged perspective view of the system shown in FIG. 1.

Referring now to FIG. 2 the details of one embodiment of the system 20 will now be described. As can be seen therein, each brace 22 basically comprises a frame-like construction consisting of an upper leg support section 32, a lower leg support section 34, and flexure means 36. Upper leg securement means 38 are mounted on the upper section 32. Lower leg securement means 40 and boot securement means 42 are mounted on the lower section 34. Adjustment means 44 is also mounted on the upper section 32.

The lower leg support section 34 is an integral, frame-like, tubular member of a general U-shape having a pair of upwardly extending leg portions 46 and an arcuate bottom portion 48. The parts of the leg portions 46 contiguous with the bottom portion 48 are denoted by the reference numeral 50 and are co-planar with the bottom portion 48. The parts of the leg portions 46 contiguous with portions 50 are denoted by the reference numeral 52 and extend at a slight angle to the plane of the portions 50. The top of the leg portions 46 are denoted by the reference numeral 54 and extend at a slight accute angle to the portions 52. The leg portions 46 of the lower section extend along the back of the calf muscle toward the medial and lateral sides of the leg. The contiguous parts 52 and 54 of each of the leg portions 46 thus produce a concavity in the brace to accomodate the calf of the skier's leg. Thus, when the lower support 34 is secured to the skier's leg, as shown in FIG. 1, with the upper end of the lower leg support section located at the calf-knee interface, the calf is comfortably fit within tne frame.

The flexure means 36 comprises a pair of flexure assemblies 58, each of which is disposed at the upper end of a respective leg portion 54 of the lower support section. The flexure assemblies will be described in considerable detail later. Suffice for now to state that each assembly includes a plurality of disk (slug)-like cylindrical segments 60 (FIGS. 10 and 11), strung on a tensioning cable 62 (FIGS. 5, 10 and 11) which is common to both assemblies and which extends through and interconnects the sections 32 and 34. The segments 60 of each assembly are arranged to pivot with respect to each other to enable the cable extending therethrough to freely bend or flex about an articulation axis perpendicular to the longitudinal axis of the cable, with the amount of pivoting being established by the tension in the cable.

As can be seen in FIG. 1 each flexure assembly 58 is located adjacent the back of the knee on a medial and lateral sides of the leg. Thus, the flexure assemblies allow the skier wearing the system to freely bend at the knee to the point at which the cable undergoes substantial tension, whereupon further flexure is precluded.

The upper support section 32 is somewhat similar to the lower section and basically comprises a pair of tubular frame members 64, each having a lower end 66 and an upper end 68. The lower end 66 of each member 64 is connected to the upper end of the associated flexure assembly 58. Each member 64 is generally linear and when the brace is secured to the leg it extends along the back of hamstring muscle toward either the medial or lateral sides of the leg (depending upon which member is involved), with the top end 68 of each member being located at the buttocks-thigh interface 70 (FIG. 1). The top end 68 of the members of each brace, as well as a web of material (to be described later) strung therebetween, form a "seat" for the skier's body.

The material forming the tubular frame sections is preferably non-resilient. One particularly suitable material comprises aluminum tubing, Type 6061T6, of 0.5 inch (12.7 mm) outside diameter, having a wall thickness of 0.083 inch (2.1 mm). While the tubing is shown as being circular in cross-section it can be of any other suitable cross-sectional shape. For example, the tubing might be flat or slightly convex at the point of contact with the leg in the interest of comfort and to provide a slimmer, trimmer appearance.

The common tensioning cable 62 extends from the tension adjustment means 44 located at the top end 68 of one of the tubular upper frame members 64, through the segments of the contiguous flexure assembly 58, the contiguous lower leg support section 34, the segments of the other (contiguous) flexure assembly 58 and the other (contiguous) frame member 56 making up the upper leg support section 32. The adjustment means 44 is arranged to set and adjust the degree of flexure provided by the flexure assemblies of the flexure means. In accordance with this invention the adjustment means can be constructed in various manners. Two types of such means are shown herein, namely, a continuous adjustment embodiment shown in FIG. 14 and a quick release embodiment shown in FIG. 5. The details of said embodiments will be described later.

The boot securement means 42 of each brace is mounted on the lower leg support section 34 contiguous with the bottom portion 48. Such mounting means is provided in the preferred embodiment of this invention to enable each brace to be stationarily mounted on the ski boot so that when the boot is secured to the ski, via a conventional ski binding, the brace in effect becomes an extension of the ski. Thus, the flexure means allow the brace to bend at the knee when desired. As the knee bends the tension in the cable builds up until it reaches a predetermined level of substantial tension which establishes the maximum flexure angle. Once the maximum flexure angle is reached the skier's weight is fully supported by the ski via the brace and its now tense flexure means. Moreover, since the amount of tension, (and hence the maximum flexure angle), is adjustable by the means 44, the skier can transfer as much of his or her body weight as desired to the skis to reduce the amount of physical effort expended during skiing. A typical flexure of the brace constructed in accordance with this invention is shown by the phantom lines in FIGS. 2 and 8.

It must be pointed out at this juncture that while the ski brace system of this invention is primarily designed for mounting directly to the ski boot, alternative arrangements can be utilized to mount the system to the binding or directly to the ski itself. Moreover, for some applications the brace can be constructed with its lower section arranged to be secured only to the lower portion of the leg of the skier and not to any portion of the ski boot, binding or ski. In such an alternative arrangement, the skier's body weight is transferred to the lower portion of the skier's leg and not to the ski itself.

As can be seen in FIG. 2 a web 80 of fabric or other flexible material is mounted spanning the frame of the brace from the top end thereof to a point just below the knee. The material web 80 includes a pair of tubular marginal side portions 82. Each tubular side portion 82 is adapted to receive therein an associated upper frame member 64, the contiguous flexure assembly 58 and the contiguous portion 54 of associated leg portion 46 of the lower leg support section. With the web 80 mounted in place as shown in FIG. 2 a hammock-like construction results for supporting the back of the skier's leg from the buttocks-thigh interface to below the knee-calf interface. This feature serves to spread out the support pressure applied by the brace over the back of the leg, thereby insuring long term wearing comfort.

The upper leg section mounting means 38 comprises a pair of straps 90 and 92 fixedly secured to the material web 80, with strap 90 being fixedly located adjacent the top of the upper section 32 for securement about the thigh just below the crotch and with strap 92 mounted approximately 5 inches (12.7 cm) to 6 inches (17.8 cm) above the knee. The lower leg securement means 40 consists of a strap 94 mounted on the web 80 approximately 4 inches (10 cm) below the knee cap. Each strap includes a conventional buckle 96 located at one end for releasable securement to the other end of the strap. In lieu of the buckles 96, VELCRO or other releasable fastening means, e.g., snaps, etc., can be used.

As mentioned earlier, when the brace is in place on the leg the upper end of the upper support section 32 (and hence the web 80 suspended between the frame members forming the upper support section) forms a seat-like construction at the buttock-thigh interface. This feature is of considerable importance to prevent the brace from riding up over the buttocks during use. Such sliding action is adverse in that it would reduce the support effect of the brace.

In the interest of comfort padding is provided in the fabric web tubular side portions 82 at the top end of the upper body support section 32.

Figure 3:
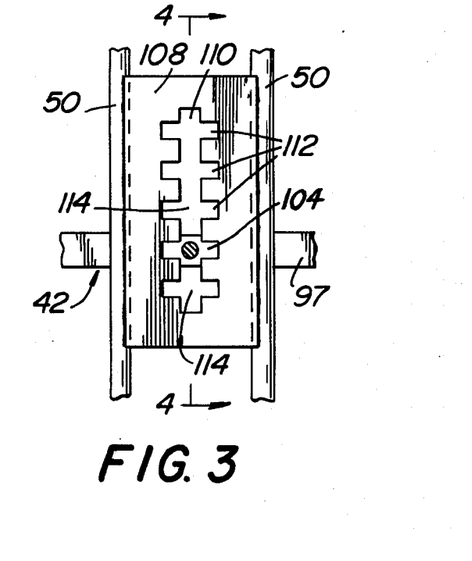
FIG. 3 is an enlarged sectional view taken along line 3—3 of FIG. 2.
Figure 4:
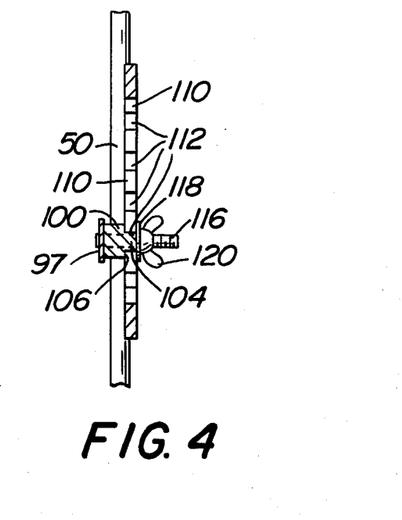
FIG. 4 is an enlarged sectional view taken along line 4—4 of FIG. 3.

In order to effect the optimal mounting of the brace on the ski boot, the boot securement means 42 is adjustable in height. The details of the securement means 42 can best be appreciated by reference to FIGS. 2, 3 and 4. As can be seen therein the means 42 basically comprises a strap 97 having a conventional hasp-type latching means 98 disposed at opposite ends thereof. A mounting block 100 is secured at a midpoint of the strap 97. The mounting plate 100 is fixedly secured to the strap 97 by a pair of rivets 102. Key means in the form of a cross-like projection 104 (FIGS. 3 and 4) extends outward from the rear surface 106 of the mounting plate 100. The key means is arranged for cooperation with means on the brace for mounting the ski boot strap at various elevations on the lower end of the brace section 34. This feature enables one to readily adjust the height of the boot securement strap on the brace to comfortably fit the leg of the skier irrespective of the length of the skier's legs. To that end a slotted plate 108 is fixedly mounted, e.g., welded, to adjacent frame portions disposed at the bottom of the brace's lower leg support section 34. The plate 108 includes an elongated, vertically oriented slot and a plurality of cross-slots 112 intersecting the vertical slot at respective equadistantly spaced heights along the vertical slot to produce respective cross-shaped openings 114. Each opening 114 is configured to closely receive the key 104 on the strap means 42. A washer 118 and an associated wing nut 120 are threadedly mounted on a bolt 122 fixedly secured to the mounting block 100 to serve as the means for locking the key in place in any particular opening 114.

Figures 10, 11:
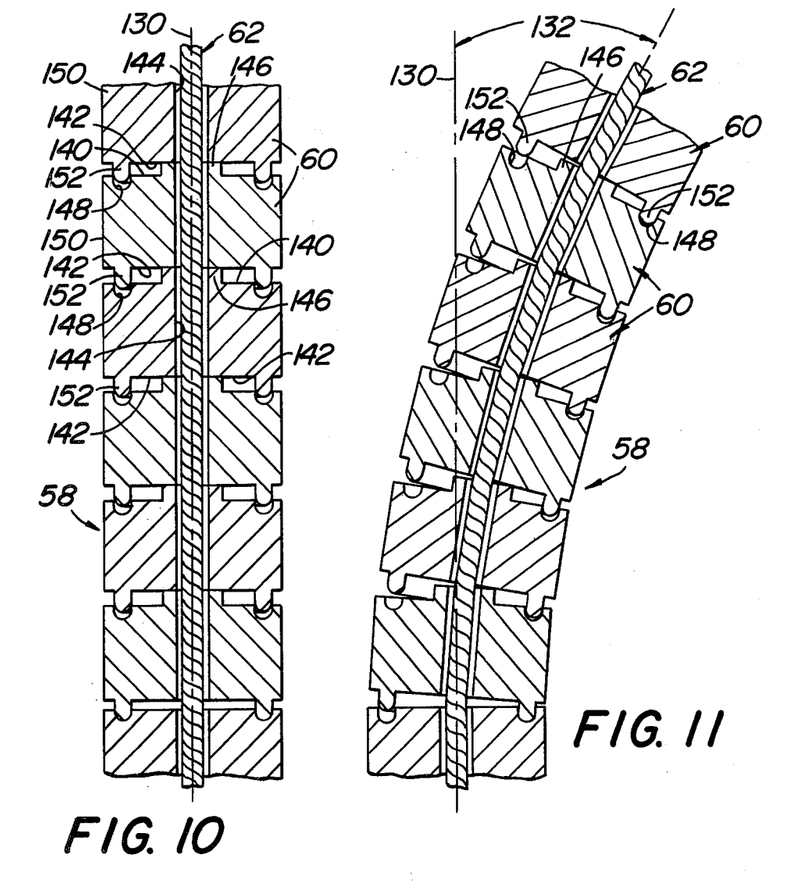
FIG. 10 is an enlarged sectional view taken along line 10—10 of FIGS. 2 and 8.
FIG. 11 is a sectional view, similar to that shown in FIG. 10, but showing the structure therein undergoing flexure.

Referring now to FIGS. 10 and 11 the details of each of the flexure assemblies 58 will be described. As mentioned heretofore, each assembly includes a plurality of disk-like segments 60 strung on a common cable 62 extending through both assemblies and tubular frame members making up the brace. The assemblies 58 are arranged to enable the skier's knee to freely flex up to a predetermined angle at which point the cable undergoes substantial tension, whereupon further flexure is precluded.

In FIG. 10 there is shown the condition of a typical flexure assembly when the skier's knee is straight. In such a case the longitudinal axis 130 of the cable 62 is linear and generally vertical. When the skier's knee is flexed, as shown in FIG. 11, the disk-like segments 60 pivot slightly with respect to each other (as will be described hereinafter) to permit the cable to flex or bend through an angle denoted by the reference numeral 132 about an articulation axis (not shown) which is disposed perpendicular to the longitudinal axis 130. The maximum angle of flexure is established by the amount of tension in the cable 62 (and hence by the setting of the adjustment means 44, to be described later) and can be anywhere within the range of approximately 0° to approximately 120°. Once the assemblies 38 have flexed through the predetermined angle flexure beyond that angle is precluded while return of the knee to a more linear orientation is freely permitted.

The assemblies 38 exhibit only slight resiliency once the maximum flexure angle is attained so that they will dampen shock yet produce very little bounce when in use on uneven terrain. The slight or residual resiliency exhibited by the flexure assemblies at the maximum flexure angle is on the order of approximately 10%.

Since the flexure assemblies and the associated frame sections are essentially non-resilient they do not produce any force on the skier's legs tending to straighten the legs, which force could result in leg instability. Hence the flexure assembly of this invention, in combination with the rigidity of the brace's frame, provides passive, adjustable support for the skier. Moreover, since the angle of flexure is adjustable through a large range and since the flexure assemblies do not impede any lateral or side motion of the knee joint, the brace can be worn without interference with normal leg motion.

In order to insure that the flexure assemblies bend uniformly and without subjecting the tensioning cable to potentially destructive shear forces, each of the segments includes surface contour features which will now be described. Thus, as can be seen each segment 60 comprises a cylindrical, disk-like member having a top surface 140, bottom surface 142 and a central, longitudinally extending passageway 144. The top surface 140 is generally planar and includes an annular mesa 146 contiguous with the central passageway 144 and projecting upward slightly, e.g., 1/64" (0.4 mm) above the surface 142. An annular, semi-circular groove or recess 148 extends into the top surface 140 immediately adjacent the periphery 150 of each segment. An annular, semi-circular ridge 152 projects downward from the bottom surface 142 of each segment. The ridge 152 is located at the same radial distance from the center of the passageway 144 as the annular recess 148. The height of the ridge 152 is slightly greater than the height of the mesa 146, but slightly less than the depth of the recess 144. Accordingly, when the skier's knee is straight, each of the segments 60 are equadistantly spaced slightly from one another as shown in FIG. 10, with the ridge of each segment being disposed slightly within the recess in the segment immediately therebelow. The slight spacing between the contiguous segments 60 insures that when the skier's knee is bent that each segment will pivot uniformly with respect to the other as shown in FIG. 11.

In operation when the bending or flexure of the assembly 58 commences, such action commences at the points of least resistance to flexure, namely the spaces between the contiguous segments. Thus, all of the spaces on the side of the segments toward the bend close together while the diametrically opposed spaces open (see FIG. 11). This action occurs uniformly. The amount of tension provided in the cable establishes the maximum amount of pivoting of the segments with respect to one another.

The mating of the ridge-groove of the contiguous segments serves to center or axially align those segments and keep them axially aligned when the assembly is bent. This action prevents any cable-fraying-inducing, segment misalignment, which could otnerwise occur if the segments could slide laterally with respect to each other.

In the interests of strength and long term reliability, the flexure assembly segments 60 are preferably formed of a strong, tough material, such as tempered steel. The height of the segments, that is the distance between the upper and lower surfaces, can be of any suitable size, although it has been found that segments in the range of approximately 5/16 inch (8 mm) to ⅝ inch (16 mm), are particularly effective. The diameter of the segments can also be of any suitable size, although segments in the range of from ⅝ inch (16 mm) to ¾ inch (19 mm) provide sufficient strength without sacrificing comfort or appearance.

Figure 5:
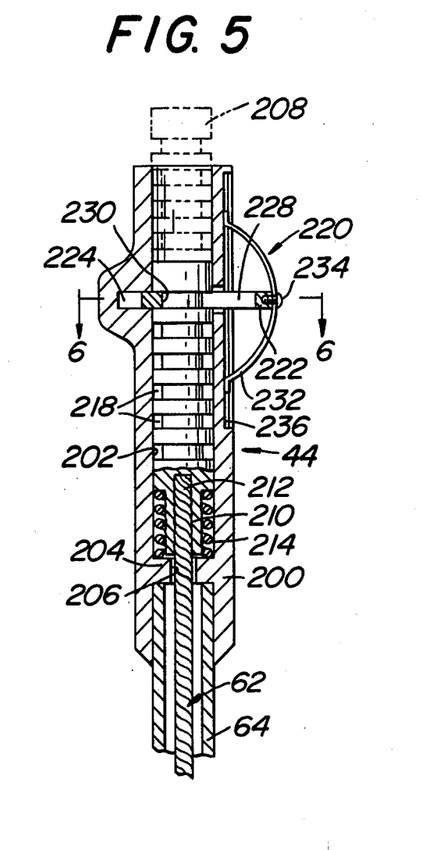
FIG. 5 is an enlarged sectional view taken along line 5—5 of FIG. 2.
Figure 6:
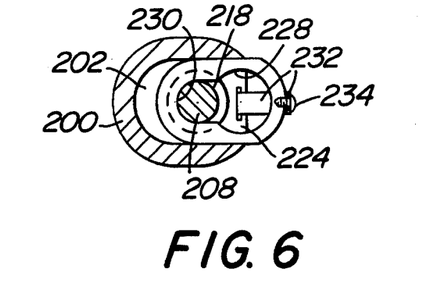
FIG. 6 is an enlarged sectional view taken along line 6—6 of FIG. 5.
Figure 7:
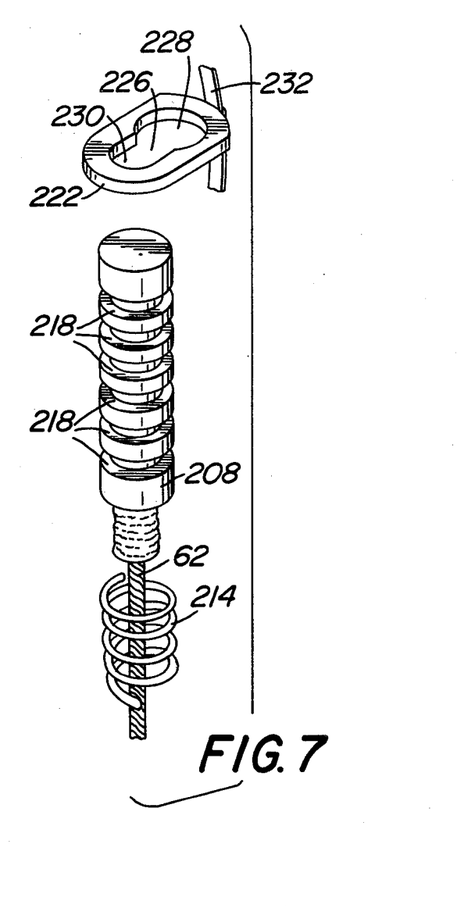
FIG. 7 is an exploded perspective view of a portion of the device shown in FIG. 5.

The means for establishing the amount of tension in the cable preferably consists of the quick acting embodiment 44 shown in FIGS. 5-7. Thus, as can be seen therein, the quick release adjustment means 44 basically comprises a housing 200 mounted on the top end of one of the frame sections 64. The housing is basically cylindrical and includes a central bore 202 bounded at the lower extremity by a bottom wall or ledge 204. A central opening 206 is provided in the wall 204. A cylindrical slide 208 is disposed within the bore 202. At the lower end of the slide 208 there is a central hole 210 into which the end 212 of the tensioning cable 62 is disposed. The cable is locked in place within the hole 210 by either a swaged or soldered connection. The other end of the cable is fixedly secured (such as by swaging) in the other tubular member of the upper leg section 32.

The diameter of the slide 208 contiguous with the hole 210 is less than the diameter of the remaining portion of the slide to provide an annular recess about which a helical compression spring 214 is disposed. The compression spring is arranged to apply an upward force to the slide to cause the slide to move, if unimpeded by means to be described hereinafter, to the phantom line position shown in FIG. 5. When the slide is in the phantom line position the maximum tension is applied to the cable 62. When the slide is in the lowermost position, shown in full in FIG. 5, that is when the return spring is compressed to its maximum, the minimum tension is applied to the cable 62.

As can be see the slide 208 includes a plurality of adjustment locking grooves 218 extending about the periphery of the slide at equadistantly spaced locations therealong.

The slide 208 is arranged to be held in any position between the fully extended (phantom line) position and the fully retracted (full line) position by the locking means to be described now. That means comprises the heretofore mentioned adjustment grooves 218 and spring-loaded adjustment lock means 220. The adjustment lock means 220 basically comprises a slide lock 222 (FIGS. 6 and 7) in the form of a planar member. The slide lock is disposed for reciprocating movement within a slot 224 in the side wall of the housing 220 and perpendicular to the longitudinal axis of the slide 208. The slide lock 222 includes a hole 226 extending therethrough. The hole 226 is made up of an enlarged diameter circular opening 228 and a smaller diameter circular opening 230. The smaller diameter opening 230 tangentially merges into the larger diameter portion 228. The diameter of the larger opening 228 is slightly greater than the maximum diameter of the slide 208, while the diameter of the smaller circular opening 230 is slightly larger than the diameter of the slide at each of the recesses 218.

When the slide lock 222 is located within the slot 224 a portion of the slide 208 extends through the opening 226. The slide lock 222 is normally maintained in the position shown in FIGS. 5 and 6 by a leaf spring 232. The leaf spring 232 consists of a bow-shaped member secured at opposite ends thereof to the housing 200 via a milled groove 236. The apex of the leaf spring 232 is located opposite to the slot 224 and is connected to the slide lock 222 via a screw 234 or other means, such as a rivet.

When the leaf spring is in its normal state, as shown in FIG. 5, the slide lock is automatically retracted slightly from the slot 224 so that the opening 230 in the slide lock is axially aligned with the center of the slide 208. The thickness of the slide lock 224 is slightly less than or equal to the width of each of the locking recesses 218 in the slide. Accordingly, when the slide lock leaf spring 232 is in the position shown in FIG. 5, the slide lock 222 is received within one of the grooves 218, thereby locking the slide 208 in place against the urging of the compression spring 214. When the leaf spring 232 is depressed radially inward, that is toward the housing 200, so that the enlarged diameter opening 228 is axially aligned with the longitudinal axis of the slide 208, the slide is free to move either up or down the bore to establish a setting for the tension cable.

The adjustment of the tension on the cable is accomplished as follows: The leaf spring is depressed by applying a force thereto, e.g., pressing on it with one's finger. This action releases the slide lock from the slide. The user then freely bends his or her knees to the position desired for skiing. This action has the effect of bending the cable and segments thereon, thereby pulling the slide against the action of the helical return spring to the equilibrium position for that particular knee angle. The leaf spring 232 is then released so that it pulls the slide lock 224 back to the locked position, whereupon the slide lock is received within that recess 218 disposed opposite the slot 224. This action effectively locks the slide in the vertical position to establish the maximum flexure angle assumed by the skier.

As will be appreciated by those skilled in the art, once the maximum deflection angle is set the skier can thereafter freely straighten his or her legs, unimpeded by the brace. In fact such knee straightening action will result in the slackening of the cable from the position set when the knees were bent.

In the interest of wearing comfort the quick release means 44 is located within surrounding padding material in the tubular sleeve 82 of the webbing 80. The leaf spring 232 extends through a slot in the webbing for ready access by the skier.

In FIGS. 8, 9, 14 and 15 there is shown an alternative embodiment of a ski brace device constructed in accordance with this invention. The device shown therein basically consists of the same structure as shown and described heretofore except for the structure of the boot securement means and the cable tensioning means. Thus, the common details of the brace shown in FIG. 8 will not be reiterated.

Figures 8, 9:
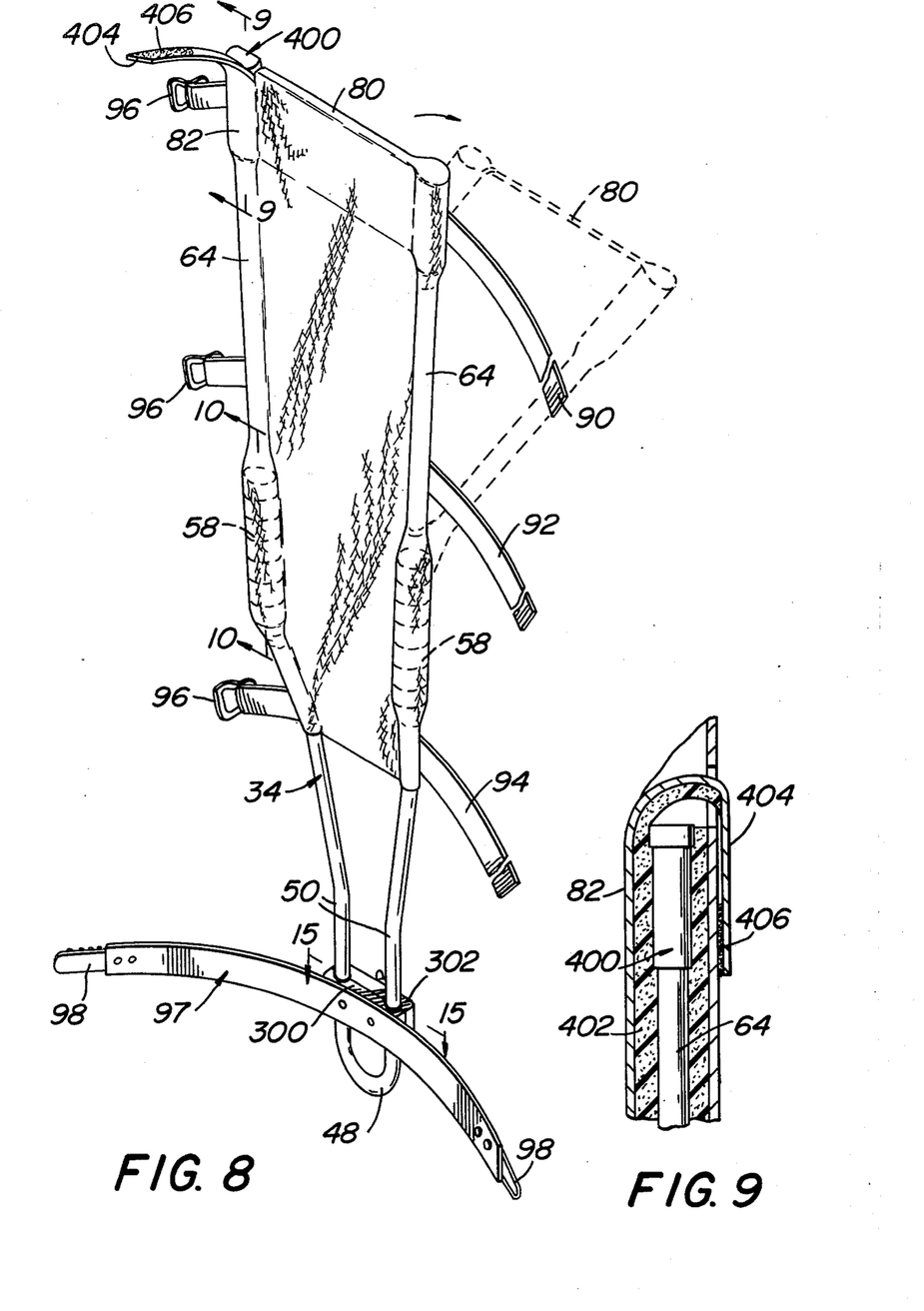
FIG. 8 is an enlarged perspective view of an alternative embodiment of the system.
FIG. 9 is an enlarged sectional view taken along line 9—9 of FIG. 8.
Figures 14, 15:
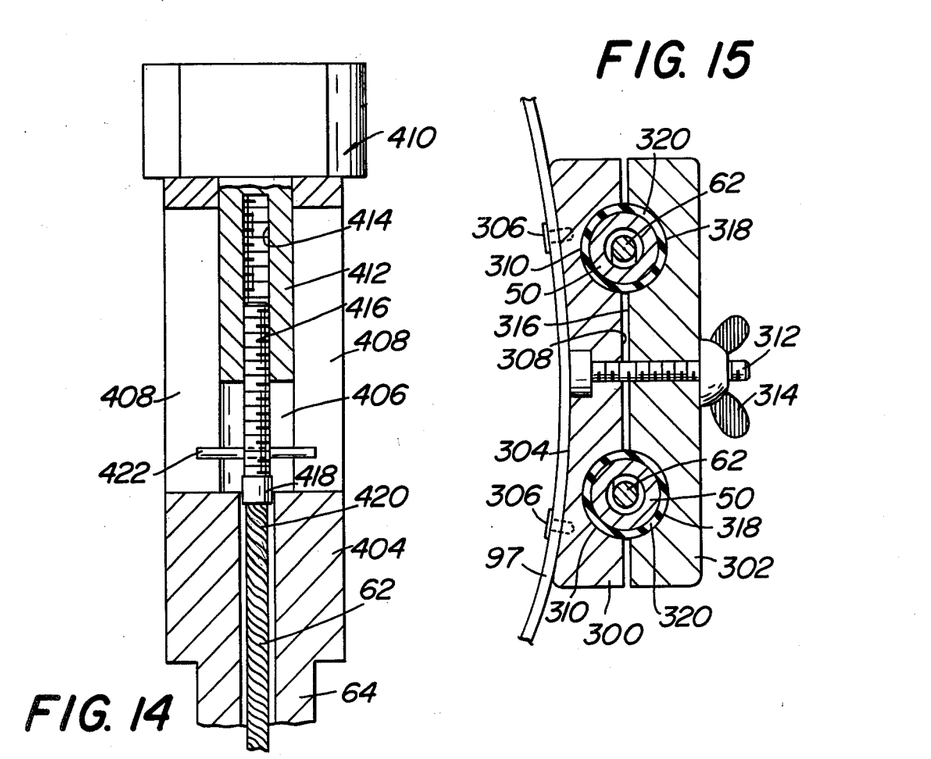
FIG. 14 is an enlarged sectional view taken along line 14—14 of FIG. 12.
FIG. 15 is an enlarged sectional view taken along line 15—15 of FIG. 8.

As can be seen in FIGS. 8 and 15 the means for adjusting the height of the boot securement strap 97 basically comprises a pair of mating blocks 300 and 302. Block 300 includes a slightly concave inner surface 304 to which the boot securement strap 97 is secured via plural rivets 306. The block 300 includes a generally planar face 308. A pair of semi-circular recesses 310 are provided in the face 308 and extend vertically from the top to the bottom of the block. The block 302 is releasably secured to the block 300 via a bolt 312 extending through those blocks and perpendicular to face 308. The block 302 is held in place on the bolt via a wing nut 314. Block 302 includes a generally planar face 316 disposed immediately adjacent to face 308. A pair of semi-circular elongated recesses 318 are provided in the front face 316 of block 302 directly opposite to the recesses 310 and block 300. A resilient material, e.g. rubber, ring 320 is disposed within recess 310 and the contiguous recess 316 on one side of the two adjacent blocks and a similar ring 320 is disposed in the contiguous recess on the other side of the block. The frame portions 50 of the lower leg assembly 34 extend through respective sleeves 320. Thus, if the wing nut 314 is loosened so that block 302 moves slightly away from block 300, the blocks may be slid along frame portions 50 to the desired height position thereon. The wing nut is then tightened to lock the boot securement means at tne desired height position.

An alternative cable tension adjusting means is shown in FIG. 14. The means shown in FIG. 14 is not of the quick adjustment type, but rather of the continuous adjustment type. That means is denoted by the reference numeral 400 (FIG. 9). The continuous tension adjusting means 400 is located within the sleeve 82 of the web 80 at the top 68 of one of the frame members 64. Padding 402 is disposed about means 400 in the interest of wearing comfort. A padded flap 404 is also provided to cover the top of the adjusting means and includes at its free end VELCRO fastening means 406 to hold the flap in place on the sleeve 82.

The tensioning means 400 basically comprises an enlarged body portion 404 disposed at the top end of member 64. The body portion 404 may be formed integrally with the member 64 and includes a central bore 406 from which a pair of diametrically opposed slots 408 extend radially outward. An adjustment cap 410 is mounted on the body 404. The adjustment cap 410 includes an enlarged head or knob from which there projects downward a cylindrical extension 412. The cylindrical extension is of a diameter equal to or slightly less than the diameter of the bore 406. A threaded hole 414 extends into the extension 412 along the central axis thereof. A threaded insert 416 is threadedly engaged in the opening 414. The threaded insert is fixedly connected by a swaged connection 418 to the upper end 420 of the common cable 62. The other end of the cable is fixedly secured within the other member 64 of the upper body support section 32. A guide pin 422 extends through the threaded member 416 and projects radially therefrom. Each end of the guide pin 422 is located within a respective slot 408 within the body 404 to prevent rotation of the insert.

The adjustment knob 410 is arranged to be rotated either clockwise or counter-clockwise. As will be appreciated by those skilled in the art, when the adjustment knob 412 is rotated in the clockwise direction the threaded member 416 is pulled deeper into the threaded bore 414, whereupon the tension in the cable is increased. Conversely when the knob 412 is rotated in the counter-clockwise direction tension in the cable is decreased. Thus, one can set the cable at the lowest tension, bend the knees to the desired orientation and thereafter tighten the adjustment knob by rotating it until further rotation is impeded by the tension on the cable. At this point the system is set for the knee angle selected.

Figure 12:
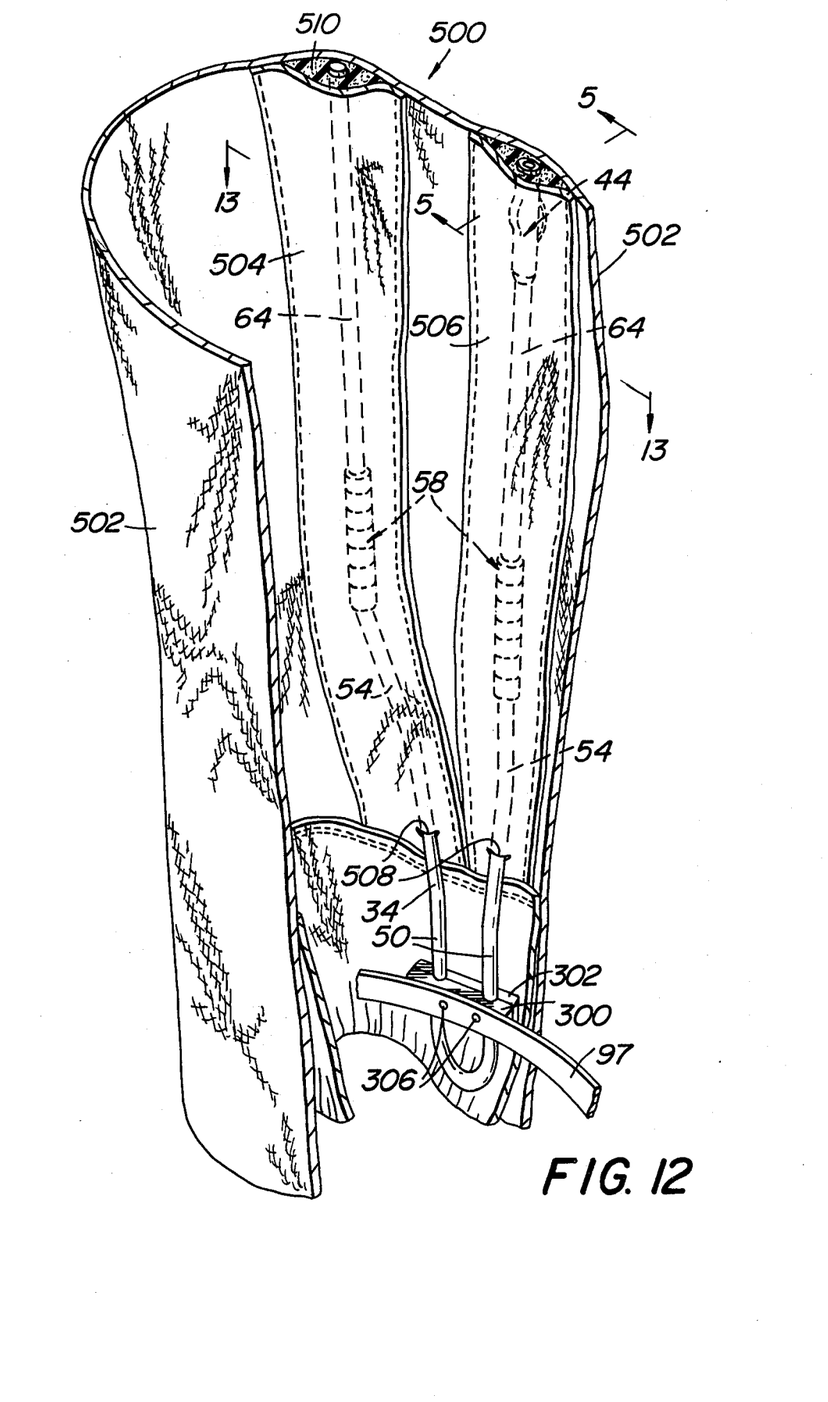
FIG. 12 is an enlarged perspective view, partially in section, showing an alternative body weight support system which is incorporated in a garment.
Figure 13:
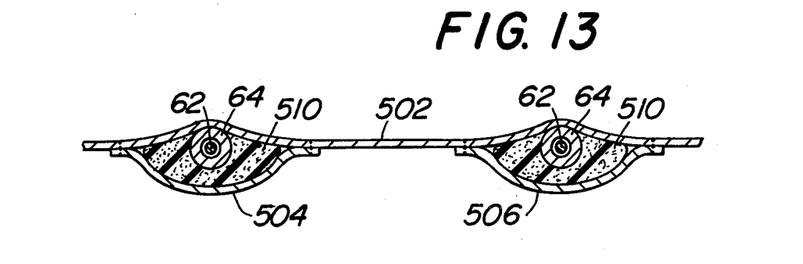
FIG. 13 is an enlarged sectional view taken along line 13—13 of FIG. 12.

In FIG. 12 there is shown an alternative embodiment of this invention. In the embodiment shown in FIG. 12 ski braces like those described heretofore are incorporated into a garment, such as a pair of ski pants 500. In the interest of drawing simplicity only a portion of the ski pants 500 is shown. The ski pants 500 basically consists of a pair of leg portions 502 (only one of which is shown) formed of any conventional fabric. Each leg portion 502 comprises a pair of longitudinally extending passageways 504 and 506 formed of respective fabric strips sewn onto the inside of the leg. Each passageway 504 and 506 is arranged to receive therein a respective portion of the ski brace frame and associated flexure means and tension adjustment means like that shown in FIG. 2. The bottom portion of the brace extends through respective openings 508 in each of the passageways so that the lower portion of the brace is exposed within the interior of the pants leg 502 for ready connection to the ski boot. In the interest of comfort padding, such as foam rubber 510, is disposed within the passageways 504 and 506 surrounding the brace sections therein.

While either of the two boot securement height adjustment means can be utilized in the embodiment shown in FIG. 12, the continuous height adjustment means, of the ski brace embodiment of FIG. 8 has been shown.

The preferred embodiment of the tensioning means used in the garment support system embodiment of FIG. 12 consists of the heretofore described quick release mechanism 44. In such a construction the quick release means 44 is disposed within the garment so that the leaf spring 232 is disposed under the outer fabric of the garment, but extending radially outward. Accordingly, all that is required to adjust the setting of the support system is to press on the fabric of the garment over the leaf spring to release the locking mechanism and thereafter bend at the knee to establish the tensioning of the cable as described heretofore.

As will thus be appreciated from the foregoing, the support system of the instant invention has a wide variety of applications other than the specifically disclosed skiing application. For example, the device can be used whenever it is desirable to provide support for a person who must stand with the knees bent in a predetermined position for an extended period of time. One example of such applications is use by farm workers for manual picking of low growing crops, inasmuch as the system can provide capability for total support of the body, while allowing complete flexibility for all normal leg and body movements, e.g., lateral bending, leg extension, walking, etc.

Insofar as the advantages of the system to skiers are concerned, the adjustment of the degree of flexure of the angle enables skiers to readily set the point at which the knee bend angle produces total support for the body, thereby resulting in weight-less skiing based on personal preference. The total support provided by the system not only relieves leg strain but also tends to center the skier's weight over the skis which is desirable for effective skiing. The non-resilient nature of the system provides proper damped, supportive force which does not oscillate or rebound, thereby insuring that the skier can maintain effective control.

The fabric web of the system spreads the body weight over a large surface on the rear side of the upper leg so there are no pressure points which would tend to be uncomfortable. Moreover, by virtue of the securement of the system to the boots, most of the body weight is transferred to the boots. Thus, the skier can "sit" on the system while remaining in a good attack posture. The resulting relaxation of the leg muscles during such operation eliminates the normal muscle strain and fatigue associated with skiing, thereby making skiing a much more pleasurable recreation.

The location of the support means halfway between the rear and side of the leg, puts the support means out of the way during a fall, since during most falls the skier either lands on the rear portion of the legs or on the side-hip area. Moreover, the supports are themselves padded. The padding of the system coupled with the location of the system on the fleshy, well-muscled areas of the leg, thus, does not present any hazard in the event that the skier does fall.

Owing to the height adjustment means for establishing the connection to the boot, the system can be utilized by skier's of various heights.

The adjustment feature of the support system of the instant invention enables one to accurately reset the system to any desired position, thereby compensating for any wear-induced changes which may occur over the long life of the system.

By virtue of the foregoing features of the instant invention, persons heretofore unable to ski due to some physical defect such as amputees, persons with muscle or nerve disorders, bad knees, etc., can ski effectively and safely. Thus, the instant invention provides for safer, more aggressive and effective skiing for all persons.

Without further elaboration, the foregoing will so fully illustrate my invention that others may, by applying current or future conditions of service.

I claim:

1. A body weight support system for releasable securement to at least one leg of a person, comprising first support means, second support means and non-resilient, flexure means, said first support means including a first portion extending along the thigh, said first support means terminating at its upper and immediately adjacent the buttocks-thigh interface to form a seat and terminating at its lower end adjacent the knee, said second support means including a second portion extending along the calf, said second support means terminating at its upper end adjacent the knee and at its lower end adjacent the foot, said flexure means being located adjacent said knee and connected between said first and second support means for permitting the person to repeatedly freely bend and unbend said knee through any angular range up to a predetermined angle of bend and for providing substantial resistance to flexure therebeyond, said first and second support means including securement means for releasably securing said system to said leg.

2. The body weight support system of claim 1 wherein said second support means is arranged to be stationarily secured to means worn on the foot.

3. The body weight support system of claim 1 wherein said flexure means is adjustable for establishing said angular range of flexure.

4. The body weight support system of claim 3 wherein said flexure means comprise plural elements coupled to one another, via tensioning means, whereupon said elements can pivot with respect to one another, with the degree of pivoting being established by said tensioning means.

5. The body weight support system of claim 4 wherein said tensioning means comprises an elongated, flexible cable on which said plural elements are strung.

6. The body weight support system of claim 5 wherein said cable is fixedly secured to one of said support means.

7. The body weight support system of claim 6 wherein said tensioning cable is connected between said first and second support means and wherein said flexure means includes adjustable means for shortening or lengthening said cable means to establish the tension in said tensioning cable.

8. The body weight support system of claim 7 wherein each of said elements is tubular and include surface means adapted to engage the immediately adjacent element to facilitate uniform pivoting of each of said elements.

9. The body weight support system of claim 1 wherein said system is arranged for use by a skier with said system supporting the skier in a centered position over a ski mounted on a boot on the skier's foot, with the skier's buttocks located over the boot and with the skier's knee forward thereof to expedite skiing.

10. The skier body weight support system of claim 9 wherein said second support means includes releasable securement means for stationarily securing said second support means to said ski boot.

11. The skier body weight support system of claim 10 wherein said flexure means is adjustable to establish said angular range.

12. The skier body weight support system of claim 11 wherein said adjustment means comprises quick acting means wherein once the knee is flexed to the desired angle, the quick acting means can be engaged to impede flexure beyond that angle.

13. The skier body weight support system of claim 11 wherein said flexure means comprise plural elements coupled to one another, via tensioning means, whereupon said elements can pivot with respect to one another, with the degree of pivoting being established by said tensioning means.

14. The skier body weight support system of claim 13 wherein said tensioning means comprises an elongated, flexible cable on which said plural elements are strung.

15. The skier body weight support system of claim 14 wherein said cable is fixedly secured to one of said support means.

16. The skier body weight support system of claim 15 wherein said tensioning cable is connected between said first and second support means and wherein said flexure means includes adjustable means for shortening or lengthening said cable means between said first and second support means to establish the tension in said tensioning cable.

17. The skier body weight support system of claim 16 wherein each of said elements is tubular and include surface means adapted to engage the immediately adjacent element to facilitate uniform pivoting of each of said elements.

18. The skier body weight support system of claim 17 wherein said adjustment means comprises quick acting means wherein once the knee is flexed to the desired angle, the quick acting means is engaged to prevent flexure beyond that angle.

19. The skier body weight support system of claim 9 wherein each of said first and second support means comprises at least one elongated frame-like member.

20. The skier body weight support system of claim 19 wherein each of said support means comprises a pair of generally parallel elongated, frame-like members having webbing means interposed therebetween for engaging an associated portion of the leg of the skier.

21. The skier body weight support system of claim 19 wherein said first and second support means and said flexure means are incorporated in a garment worn on the leg.

22. The skier body weight support garment of claim 21 wherein said releasable securement means comprises strap means arranged for stationarily mounting said second support means on said ski boot.

23. The skier body weight support system of claim 20 wherein said first support means includes strap means for strapping said first support means to the thigh just below the buttocks and just above the knee and wherein said second support means includes strap means for strapping said second support means to the calf just below the knee.

24. The body weight support system of claim 23 wherein said strap means for securing said second mounting means to said boot is adjustably mounted on said second support means to provide an optimal interface with said boot.

25. The skier body weight support system of claim 9 wherein said flexure means includes adjustment means located adjacent the upper end of said first support means for establishing said predetermined angular flexure range.

26. The skier body weight support system of claim 9 wherein said first and second support means and said flexure means are arranged to be worn over a garment on the leg.

27. The skier body weight support system of claim 9 wherein said first and second support means and said flexure means are incorporated in a garment worn on the leg.

* * * * *